United States Patent [19]

Scher

[11] Patent Number: 4,714,614

[45] Date of Patent: Dec. 22, 1987

[54] PROCESS FOR INDUCING SUPPRESSIVENESS TO FUSARIUM VASCULAR WILT DISEASES

[75] Inventor: Frances M. Scher, Fort Collins, Colo.

[73] Assignee: Colorado State University, Fort Collins, Colo.

[21] Appl. No.: 665,096

[22] Filed: Oct. 29, 1984

Related U.S. Application Data

[63] Continuation of Ser. No. 335,895, Dec. 30, 1981, abandoned.

[51] Int. Cl.$^4$ ............................................. A01N 63/00
[52] U.S. Cl. ....................................................... 424/93
[58] Field of Search ......................................... 424/93

[56] References Cited

U.S. PATENT DOCUMENTS 4,489,161 12/1984 Papavizas .............................. 424/93

OTHER PUBLICATIONS

Dupler et al. Effect of Synthetic Iron Chelates on Population Densities of *Fusarium–oxysporum* and *Pseudomonas–putida* in soil Phytopathology 72(7) 1982.
Fran M. Scher and Ralph Baker, "Influence of *Pseudomonas Putida* and Synthetic Iron Chelates on Fusarium Wilt Diseases", Phytopathology, vol. 72 (7), Jul. 1982, p. 986.
"Mechanism of Biological Control in Fusarium-Suppressive Soil," F. M. Scher and R. Baker, Phytopathology, 70, pp. 412–417 (1980).
"Effect of *Pseudomonas putida* and a Synthetic Iron Chelator on Induction of Soil Suppressiveness to Fusarium Wilt Pathogens," F. M. Scher and R. Baker, Phytopathology 72: 1567–1573 (1982).

*Primary Examiner*—Jerome D. Goldberg
*Assistant Examiner*—John M. Kilcoyne
*Attorney, Agent, or Firm*—Gale F. Matthews; Richard C. Stewart, III

[57] ABSTRACT

Compositions comprising a *Fusarium oxysporum* suppressing amount of one or more *Fusarium oxysporum* disease suppressants selected from the group consisting of a *Fusarium oxysporum* growth suppressing strain of *Pseudomonas putida* having the identifying characteristics of NRRL B-15001, one or more *Fusarium oxysporum* disease suppressing ferric iron chelating agents and the corresponding chelates of such agents, and methods of using such compositions for the control of *Fusarium oxysporum* wilt disease in plants.

25 Claims, 3 Drawing Figures a ~ 200 p OF FUSARIUM OXYSPORUM PER GRAM OF SOIL.

b ~ 200 p OF FUSARIUM OXYSPORUM AND $10^7$ cfu OF PSUEDOMONAS PUTIDA PER GRAM OF SOIL.

PROCESS FOR INDUCING SUPPRESSIVENESS TO FUSARIUM VASCULAR WILT DISEASES

This application is a continuation of application Ser. No. 335,895 filed Dec. 30, 1981, now abandoned.

BACKGROUND OF THE INVENTION

1. Field of the Invention

This invention relates to a novel process for control of Fusarium vascular wilt diseases and compositions for use in such a process. More particularly, this invention relates to such a process in which suppressiveness to such diseases is induced in Fusarium wilt conducive soil by adding to such soil a Fusarium wilt suppressive amount of a Fusarium wilt suppressive strain of the microorganism *Pseudomonas putida*, one or more Fusarium wilt suppressive ferric iron chelating agents, one or more of the ferric iron chelates of such agents or a combination thereof, and compositions for use in such process.

In a more limited aspect, this invention relates to a biologically pure culture of the heretofore unknown Fusarium wilt suppressive strain of *Pseudomonas putida*.

2. Prior Art

Vascular wilt diseases induced by the fungus *Fusarium oxysporum* are of considerable economic importance, annually causing millions of dollars worth of damage to important economic crops. Vascular wilt diseases occur on a wide variety of economic crops, including tomatoes, peas, bananas and cotton, often resulting in a considerable decrease in crop yields. Typically, depending on the environment and the severity of the disease, when plants become infected with these diseases, they become yellow, wilt and may eventually die if not promptly treated. The various forms of *Fusarium oxysporum* which are pathogenic to a large number of crops are widespread. Spores of the fungus are difficult to eradicate, and can survive in agricultural soils for many years.

Heretofore, several methods have been proposed for controlling vascular wilt diseases caused by *Fusarium oxysporum*. For example, various chemical methods have been suggested and several now enjoy widespread use. Although relatively effective, such chemical methods suffer from several inherent disadvantages. One such disadvantage relates to economies of obtaining an acceptable level of fungus control. Chemical control of Fusarium induced wilt diseases is expensive, and, therefore, can be used economically only in high income applications. Another such disadvantage relates to the level of control which can be obtained through use of chemical methods. Many of the various chemical fungicides that are recommended for use, such as benomyl, thiophantemethyl and thiobendozole are not sufficiently effective for widespread commerical use. Moreover, as disclosed in Erwin, D. C. 1977, *Control of Vascular Pathogens*, Pages 163–224 in: M. R. Siegal and H. D. Sister, eds. antifungal compounds, L. Manel Rekken Inc., New York, still another disadvantage is that these chemical fungicides have various physical and biological properties that greatly limit their effectiveness.

Eradication of Fusarium wilt pathogens by application of steam and various soil fumigants has also been recommended. Relatively effective short-term control is achieved by these procedures, especially if steaming is combined with the use of a fumigant such as metam sodium. However, one disadvantage of the procedure is the lack of long-term control because the pathogens survival structures (chlamydospores) are at such depth in the soil that complete eradication is almost impossible.

Several investigators have evaluated soils which are naturally suppressive to certain plant diseases, including Fusarium wilt diseases. In one such evaluation, various un-identified fluorescent psuedomonads were implicated as the suppressive factor in wheat take-all decline soil. In another such evaluation in Sher, F. M. and R. Baker, "Mechanism Biological Control in Fusarium - Suppressive Soil", Phytopathology, 70: pp. 412–417 (1980) experiments were described in which addition of a certain fluorescent pseudomand identified only as Pseudomonas sp., which had been isolated from Fusarium wilt suppressive soil, rendered *Fusarium oxysporum* conducive Fort Collins clay loam suppressive to Fusarium wilt of flax. Similarly, various non-Psuedomonad strains isolated from take-all decline soil have been reported in Kloepper, J. W., J. Leong, M. Teintze, M. Schroth, "Enhanced Plant Growth by Siderophores Produced by Plant Growth Promoting Phizobacteria", Nature 286; pp 885–886 (1980), as controlling take-all of wheat, and other non-Psuedomonad microbe strains have been shown to control Fusarium wilt in flax.

SUMMARY OF THE INVENTION

Figure 1:
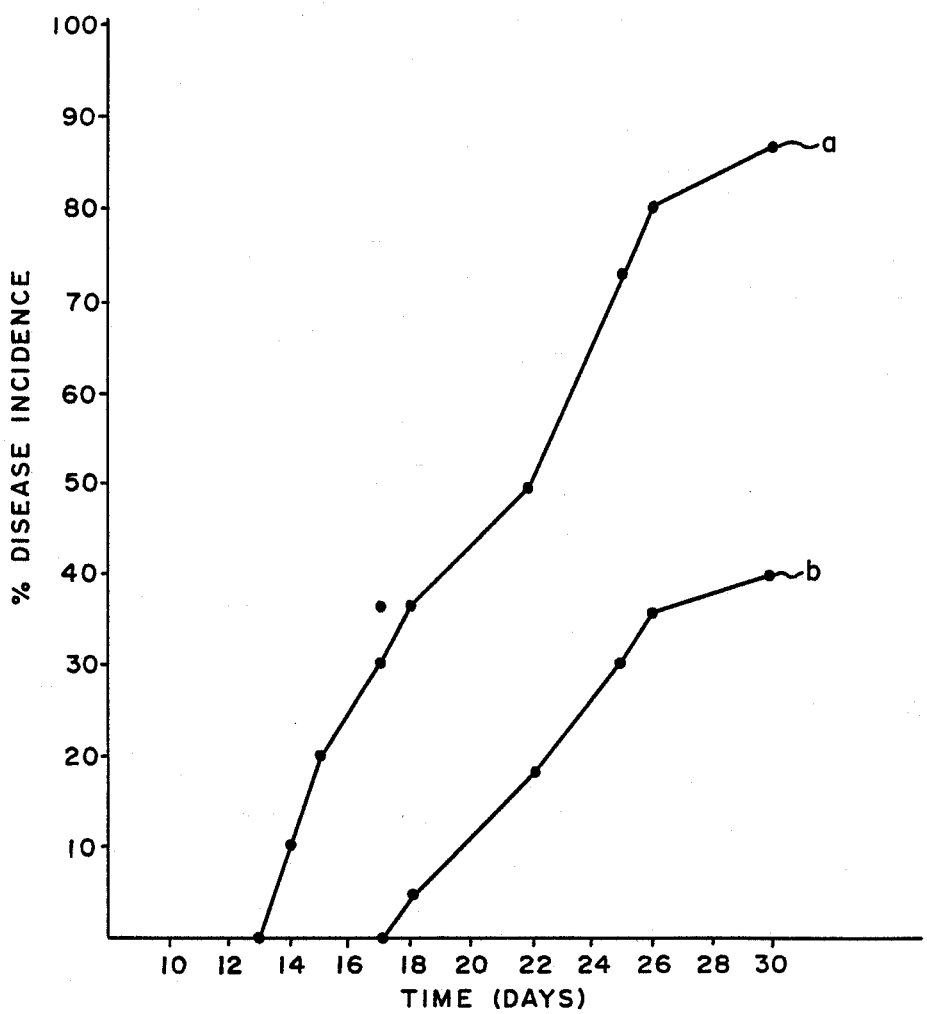
FIG. 1 is a disease progress curve of the incidence of Fusarium wilt of cucumbers versus time.

In accordance with this invention there is provided a new and useful process for suppressing *Fusarium oxysporum* wilt diseases in soil which is conducive to the growth of such plant pathogens and composition for use in such process. The process of this invention comprises applying to such soil a *Fusarium oxysporum* disease suppressing amount of one or more *Fusarium oxysporum* growth suppressants selected from the group consisting of the *Fusarium oxysporum* disease suppressing strain of the microorganism *Pseudomonas putida*, one or more *Fusarium oxysporum* disease suppressive ferric iron chelating agents, and one or more ferric iron chelates of such agents.

DESCRIPTION OF THE PREFERRED EMBODIMENTS

The microorganism employed in the process of this invention is a *Fusarium oxysporum* disease suppressing strain of the microorganism *Pseudomonas putida*. The micoorganism strain was isolated from a soil sample from the Salinas Valley, Calif. The microorganism strain was characterized by its cultural and biochemical characteristics as a strain of *Pseudomonas putida*. One of such identifying characteristics is that the microorganism produced a fluorescent pigment on King's Medium B. Another of the taxonomic characteristics identifying the microorganism as a strain of *Pseudomonas putida* is that the microorganism would not grow at 41° C. but did grow at a temperature of 22° C. to 30° C. The microorganism was an aerobe and did not hydrolyze gelatin. Furthermore, the microorganism strain utilized valine as a carbon source, but did not utilize treholose as a carbon source. The above taxonomic characteristics classify the microorganism as a strain of *Pseudomonas putida* according to Table 7.1 of the Shorter Bergey's Manual of Determinative Bacteriology p. 356, Holt, J. G. ed (1977), 8th Edition, The Williams and Wilkins Co., Baltimore Md. A subculture of this microorganism has been deposited in the permanent collection of the Northern Regional Research Laboratories, Agricultural Research Services, U.S. Department of Agriculture, Peoria, Ill., USA, under the accession number NRRL B-15001. The permanency of the deposit of this culture, and ready accessibility thereto by the public are afforded throughout the effective life of the patent in the event the patent is granted. Access to the culture is available during pendency of the application under 37 CFR 1.14 and 35 USC §112. All restrictions on the availability to the public of the deposited culture will be irrevocably removed upon granting of a patent.

In the process of this invention, the microorganism can be used in an impure state in combination with other materials which will not substantially interfere with the *Fusarium oxysporum* disease suppressing characteristics of the microorganism, or in the form of a "biologically pure culture". As used herein, "a biologically pure culture" refers to a culture of the microorganism which does not include other materials which are normally found in soil in which the microorganism grows and/or from which the microorganism is isolated. In the preferred embodiments of this invention (where the microorganism is used as the suppressant), the microorganism is preferably used in combination with one or more ferric iron chelates and/or one or more the ferric iron chelating agents, and optionally with other agricultural chemicals which are not biocidal with respect to the microorganism. Other *Fusarium oxysporum* disease suppressive materials which are useful in the conduct of this invention are *Fusarium oxysporum* growth suppressive ferric iron chelates and/or the corresponding ferric iron chelating agents. As used herein, "ferric iron chelating agents" are complexing or chelating agents which are capable of forming a chelate or complex with ferric iron cations in the soil in which the suppression of the growth of *Fusarium oxysporum* is desired, and "ferric iron chelates" are the corresponding chelates or complexes of such agents. While we do not wish to be bound by any theory, or to have the scope and spirit of this invention limited in accordance therewith, it is believed that such chelating agents and corresponding chelates function by tying up ferric iron in the soil thus preventing its uptake by *Fusarium oxysporum* present therein, while at the same time, allowing the uptake of ferric iron by plants growing in the soil. Thus, it is believed that any ferric iron chelating agent or chelate which will function as above may be employed in the conduct of this invention.

In the preferred embodiments of this invention, ferric iron chelating agents which are "ferric iron specific" (and chelates thereof) are employed. As used herein "ferric iron specific" means that such agents bond preferentially with ferric iron as contrasted with other metal ions, such as magnesium, zinc and the like, which may also be in the soil. Another characteristic of chelating agents which are employed in the preferred embodiments of this invention is that such agents will form ferric iron chelates which are stable at the pH ranges present in the soil in which the suppression of the incidence of *Fusarium oxysporum* disease is desired. In the particularly preferred embodiments of this invention, useful ferric chelating agents are selected from the group consisting of agents which form ferric iron chelates having stabilities equal to or greater than the stability of the ferric iron chelate of ethylene diamine tetraacetic acid under the environmental conditions in which the composition and/or process of this invention are used. Ferric iron chelates of such agents are also particularly preferred. Amongst these particularly preferred agents, most preferred are those which form ferric iron chelates having stabilities which are equal to or greater than the stability of the ferric iron chelate of sodium ethylenediamine di-(o-hydroxyphenylacetate), when subjected to the environmental conditions in which the composition and/or process of this invention are to be used. Ferric non-chelates of such agents are also most preferred. Illustrative of such most preferred chelating agents are oxalic acid, 2,3-dimercaptopropan-1-ol, cysteine, N,N'-di-(2-aminoethyl) ethylene diamine, pyridine-2-carboxylic acid, N,N-bis-2-hydroxyethylglycine, 8-hydroxyquinazoline, 8-hydroxyquinoline, 5-bromo-8-hydroxyquinoline, 8-hydroxy-5-idoquinoline, 5-fluoro-8-hydroxyquinoline, 8-hydroxyquinoline-5-sulphonic acid, 8-hydroxy-7-idoquinoline-5-sulphonic acid, 5-cyano-8-hydroxyquinoline, 5-formyl-8-hydroxyquinoline, 8-hydroxy-5-methylquinoline, NNN'N'-tetra(phosphomethyl)cyclohexane-1,2-diamine, ethyl-8-hydroxyquinoline-5-carboxylate, diethylenetriamine-N,N,N',N'',N''-penta-acetic acid, N-(o-hydroxy cyclohexyl) ethylenediamine-N,N',N'-triacetic acid, 4,5-dihydroxy-3-phenylazonaphthalene-2,7-disulphonic acid, N,N'-ethylene-di-(α-O-hydroxyphenyl) glycine, N,N'-ethylene-di-[-N-(2-pyridylmethyl) glycine], Desferri-ferrioxamin B, Desferri-ferrichrome, Desferri-ferrioxamin E, N-acetyl-desferri ferrioxamin B, Iron-free ferrichrome, Desferri-ferrichrysin, 2'',6''-dichloro-4'-hydroxy-3,3'-dimethyl-3''-sulphofuchsome-5,5'-dicarboxylic acid, 3,5-disulfopyrocatechol, ethylene bis-N,N'-(2-aminoethyl)-pyridine-N,N'-diacetic acid, N-hydroxyethylethylenediamine triacetic acid, diethylenetriamine penta-acetic acid, N,N-dihydroxy ethylglycine, sodium 2,3-dihydroxy naphthalene-6-sulfonate, disodium 1,2-dihydroxy benzene-3,5-disulfonate, 5-sulfosalicylic acid, and the like.

As was noted hereinabove, the *Fusarium oxysporum* suppressing strain of *Pseudomonas putida*, one or more ferric iron chelating agents and one or more ferric iron chelates can be used individually or in any combination. Because of convenience in use and greater effectiveness in a variety of soils and climates, the ferric iron chelating agent and ferric iron chelate, either individually or in combination, are preferred.

In the process of this invention a "*Fusarium oxysporum* disease suppressing amount" of one or more of the above described suppressants is added to "*Fusarium oxysporum* conducive soil*". As used herein, "*Fusarium oxysporum* conducive soil" is any soil which is conducive to the growth of any form of *Fusarium oxysporum*, and a "*Fusarium oxysporum* disease suppressing amount" is an amount of one or more of the suppressants which is sufficient to suppress *Fusarium oxysporum* wilt disease in such soil, and preferably also to suppress the incidence of such disease in a plant to any extent. Ideally, the amount of suppressant added would be sufficient to suppress substantially all growth, and such represents the preferred amounts. However, due to soil conditions, climate, addition of agricultural chemicals and other factors known to those of skill in the art, it may be that suppression of substantially all growth may not be attainable; thus, it should be appreciated that embodiments which provide only incomplete suppression are within the scope of this invention.

Because of these known factors which affect the efficacy of agricultural control agents applied to an open environment, the amounts of suppressant added to the soil will vary widely. Normally, in those embodiments of this invention where the *Fusarium oxysporum* suppressant strain of *Pseudomonas putida* is employed as the *Fusarium oxysporum* disease suppressant, the soil immediately surrounding the plant to be protected from *Fusarium oxysporum* is inoculated with at least about $10^3$ microorganism cells per gram of soil. As used herein, "immediately surrounding the plant" refers to an area up to about a 10 to 15 ft. radius from the plant to a depth of up to about 2 to 3 feet. In the preferred embodiments, the soil will be inoculated with from at least about $10^7$ cells per gram of soil, and in the particularly preferred embodiments the soil will be inoculated with at least about $10^9$ cells per gram of soil. Amongst these particularly preferred embodiments, most preferred are those embodiments wherein at least about $10^{12}$ cells per gram of soil is employed.

In those embodiments wherein one or more ferric iron chelates and/or one or more ferric iron chelating agents are the *Fusarium oxysporum* disease suppressants of choice, the total amount of such suppressants employed is preferably at least about 50 ppm of suppressant per each part of soil immediately surrounding the plant; and in the particularly preferred embodiments, at least about 100 ppm of suppressant per each part of soil is employed. In these particularly preferred embodiments, the upper level of the amount of suppressant employed is not critical, and is governed primarily by the cost of the suppressant. Amongst these embodiments, most preferred are those in which the amount of suppressant employed is in the range of from about 100 ppm to about 10,000 ppm of suppressant per each part of soil.

The biologically pure cultures of *Pseudomonas putida* employed in the process of this invention can be isolated from soil samples and can be manufactured in quantity employing standard fermentation techniques. For example, plant seed, as for example, radish, cucumber and the like can be planted in *Fusarium oxysporum* suppressive soil from the Salinas Valley. The plants are allowed to grow for a week and then are pulled from the soil. The roots are rinsed with water and the water placed on Kings B medium and allowed to grow for 24 hours. The biologically pure culture so isolated can be grown in quantity employing conventional techniques.

Cultivation of *Pseudomonas putida* can be effectuate in both liquid and solid nutrient media at a temperature of 22° to 30° C. It is to be understood also that for the preparation of limited amounts of the microorganism surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include corn steep liquor, yeast, autolyzed brewer's yeast with milk solids, soybean meal, cottonseed meal, cornmeal, milk solids, pancreatic digest of casein, distillers' solids, animal peptone liquors, fishmeal, meat and bone scraps, and the like. Combinations of these carbon and nitrogen sources can be used advantageously. Trace metals, for example, zinc, magnesium, manganese, cobalt, iron, and the like, usually need not be added to the fermentation media since tap water and unpurified ingredients containing such trace metals are used as media components.

When growth of the microorganism is carried out in large vessels, it is desirable to produce a vegetative inoculum in a nutrient broth culture by inoculating this broth culture with an aliquot from a soil or a slant culture. When a young, active vegetative inoculum has thus been secured, it is transferred aseptically, to large vessels or tanks.

The ferric iron chelating agents and their chelate derivatives useful in the conduct of the process of this invention are well known compounds, and methods for their preparation will not be described herein in detail. Such chelating agents and derivatives are readily available from commercial sources, or can be manufactured according to well known preparative techniques.

The *Fusarium oxysporum* suppressive strain of *Pseudomonas putida*, one or more ferric iron chelating agents, one or more of the corresponding ferric iron chelates of such agents or mixtures thereof can be applied to the soil and formulated into compositions according to methods known to those of skill in the art. For example, the microorganism, ferric iron chelate and/or ferric iron chelating agents can be formulated in the composition of this invention which will usually comprise a biologically compatible carrier and/or diluent, either liquid or solid, in combination with a *Fusarium oxysporum* disease suppressive amount of one or more of these active ingredients. As used herein, "biologically compatible" refers to those carriers and/or diluents or other components which will not interfere with the ability of *Pseudomonas putida*, useful ferric iron chelates and/or useful ferric iron chelating agents from suppressing the growth of *Fusarium oxysporum* as desired.

Suitable liquid diluents or carriers for use in the conduct of this invention include water, petroleum distillates, or other liquid carriers, with or without various dissolved salts or, in the case of chelating agents or chelates, suitable dissolving agents such as acids, bases, surface active emulsifying and dispersing agents. Liquid compositions may be prepared by dissolving or dispersing (whichever is applicable) a *Fusarium oxysporum* suppressing amount of one or more ferric iron chelating agents, one or more ferric iron chelates and/or the pure or impure *Pseudomonas putida* in an appropriate biologically compatible diluent or carrier.

Solid compositions can be prepared by dispersing the desired suppressants in and on an appropriately divided solid carrier such as clay, talc, bentonite, diatomaceous earth, fuller's earth and the like. When such formulations are used as wettable powders, biologically compatible dispersing agents such as liquosulfonates and various non-ionic, anionic, amphoteric or cationic dispersing and emulsifying agents can be used.

The compositions contemplated herein prevent attack by Fusarium wilt diseases upon plants or other material to which these compositions are applied, and they have relatively high residual toxicity. With respect to plants, they have a high margin of safety in that when used in sufficient amounts to supress or prevent Fusarium wilt disease, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable *Fusarium oxysporum* growth suppressing characteristic of of the compositions or impart undesirable characteristic for instance, phytotoxicity, to the compositions. The compositions are so chemically inert that they are compatible with substantially any other constituents of the spray schedule, and they may be used in the soil, upon the seeds, or the roots of plants without injuring either the seeds or roots of plants. They may also be used in combination with biologically compatible pesticidally active compounds as for example, herbicides, nematocides, fungicides, insecticides and the like. It will be appreciated that the compounds of this invention can also be used in combination with other biologically active compounds or substances which affect the growth processes of plants, such as fertilizers, plant growth regulants and the like, provided that such compounds or substances are biologically compatible.

The following specific example are presented to more particularly illustrate the invention and should not be construed as a limitation thereon.

EXAMPLE I

Isolation of Pseudomonas Putida

Flame-proof nylon screens (2 cm) with 1 mm holes were placed on a *Fusarium oxysporum*-selective medium, five per petri plant. *F. oxysporum* f.sp.lini was introduced into the center of each plate. After 7 days the screens were covered with hyphae and spores of the fungus were peeled from the agar surface and buried in either Fort Collins clay loam or Metz fine sandy loam. After 24 hr. the screens were retrieved and placed in two 1-L Erlenmeyer flasks, one for each soil type, and rinsed for 15 min by circulating distilled water into the flasks through tubing inserted in rubber stoppers in the necks of the flasks. The water circulated through the flasks was flushed out through additional glass tubes in the stoppers. By this rinsing method, most extraneous soil, and microorganisms only coincidently associated with the thallus, were removed from the nylon screens, presumably leaving a high proportion of those intimately associated with the pathogen. Screens were placed on potato dextrose agar (PDA). After 24 hours bacteria and fungi were observed around the nets; bacterial growth was more abundant. Individual colonies of bacteria were streaked on PDA (to ensure purity of culture), transferred to PDA slants, and incubated at $25°\pm1°$ C. Isolates were washed from the slants with 10% skim milk and lyophilized for storage.

EXAMPLE II

The greenhouse experiments demonstrating the effectiveness of *Pseudomonas putida*, ferric iron chelates, ferric iron chelating agents and mixtures thereof in control of various species of *Fusarium oxysporum* were performed in a large growth room maintained at $28°$ C.$\pm2°$ C. Continuous fluorescent illumination was supplied at approximately 5000 lux.

Various forma specials of *Fusarium oxysporum* were prepared for addition to soil as follows: About 250 g of the carnation tissue was autoclaved with 25 ml of distilled water in 1 L flasks plugged with cotton. *Fusarium oxysporum* infected plants were touched with a sterile needle, and the needle was in turn contacted with the sterile tissue in the flask, thereby aseptically transferring the pathogen to the tissue culture in the flask. The pathogens were grown separately in these flasks at $25°$ C.$\pm1°$ C. for approximately 28 days. Tissue then was removed from the flasks and air dried. This inoculum mix was triturated in a Waring Blendor (Model 5011, Waring Products, New Hartford, Conn. 06057), passed through a 1-mm screen, and stored in plastic containers until needed. This inoculum contained macroconidia, microconidia, and chlamydospores. On each of 2 days in succession, various species of *Fusarium oxysporum* were added to raw soil and evenly mixed in a twin-shell blender. Raw portions of the inoculated soil were added to plastic pots, 250 g each, forming five control plastic pots to which *Pseudomonas putida* was not added. Other portions of the infested soil were added to other plastic pots and were inoculated with varying amounts of *Pseudomonas putida* as follows:

For introduction of the bacteria into soil, lyophilized cultures were rehydrated and shake cultured in Kings B medium for 24 hours. The bacterial cells were removed from the culture medium by centrifugation at 20,200 g and rinsed twice in physiological saline solution (0.1 m $MgSO_4$). These bacterial cells suspended in physiological stock solution were kept in a refrigerator at $10°$ C. until they were introduced into soil. The number of bacterial cells per milliliter in the stock solution was determined by plating serial dilutions on PDA. Bacteria was added to the soil by suspending the appropriate amount of stock solution in 100 ml of physiological saline and distributing this evenly into 1,000 g of soil. Appropriate amounts of selected chelating agents and chelates were added by dissolving or suspending the materials in water and distributing appropriate amounts of the resulting solutions or suspensions in the soil in the pots. Experimentation indicated that the chelating agents were sometimes insoluble in water and various artificial means, as for example, dissolving the agent in base solution can be used to increase the solubility.

Radish, cucumber and flax were planted in the pots. The physical parameters of these experiments are set forth in the following Table I as follows:

TABLE I

| Pot | Amount of Fusarium Oxysporum | Amount of P. Putida | Plant | Amount of EDDHA per g of soil | Amount of FeEDDHA per g of soil | Amount of FeEDTA per g of soil |
|---|---|---|---|---|---|---|
| A. | 50 p/g[1] | $10^7$ cfu[2]/g | radish | — | — | — |
| B. | 100 p/g | $10^7$ cfu/g | radish | — | — | — |
| control | 50 p/g | — | radish | — | — | — |
| control | 100 p/g | — | radish | — | — | — |
| C. | 200 p/g | $10^7$ cfu/g | cucumber | — | — | — |
| control | 200 p/g | — | cucumber | — | — | — |
| D. | 1000 p/g | $10^7$ cfu/g | flax | — | — | — |
| control | 1000 p/g | — | flax | — | — | — |
| E. | 1000 p/g | $10^7$ cfu/g | flax | 100 ppm | — | — |

TABLE I-continued

| Pot | Amount of Fusarium Oxysporum | Amount of P. Putida | Plant | Amount of EDDHA per g of soil | Amount of FeEDDHA per g of soil | Amount of FeEDTA per g of soil |
|---|---|---|---|---|---|---|
| F. | 1000 p/g | 10⁷ cfu/g | flax | — | 100 ppm | — |
| G. | 1000 p/g | 10⁷ cfu/g | flax | — | — | 100 ppm |
| H. | 1000 p/g | — | flax | 100 ppm | — | — |
| I. | 1000 p/g | — | flax | — | 100 ppm | — |
| J. | 1000 p/g | — | flax | — | — | 100 ppm |

Figure 2:
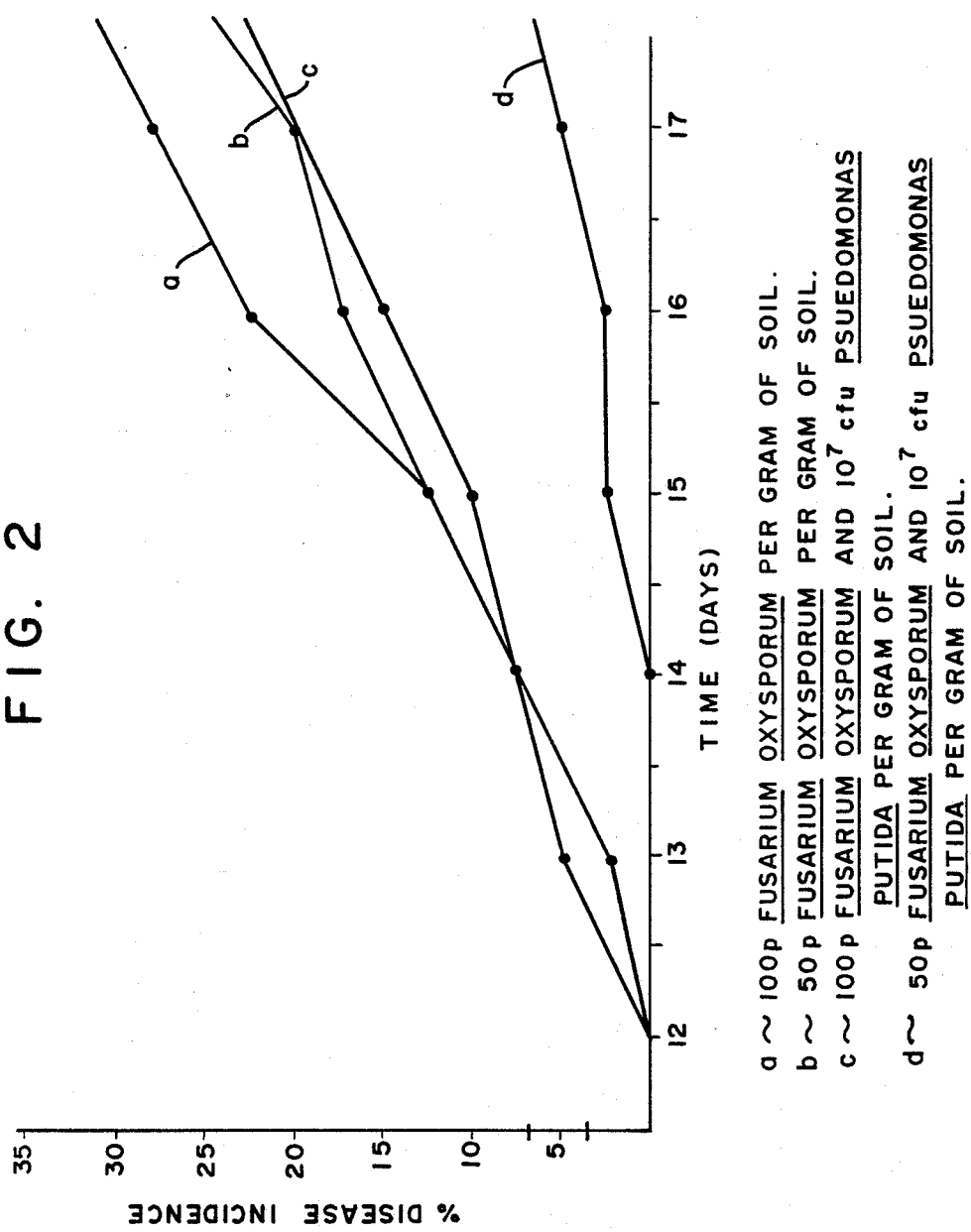
FIG. 2 is a disease progress curve of the incidence of Fusarium wilt in radish.

[1] "p/g" is propagules of fungus per gram of soil.
[2] "cfu" is cells of microorganism per gram of soil Every few days the plants were evaluated to determine the extend of *Fusarium oxysporum* infection. The incidence of Fusarium wilt of radish, cucumber and flax after 30 days is set forth in FIGS. 1, 2 and 3. FIG. 1 illustrates a disease progress curve for Fusarium wilt of cucumber. From the results set forth in FIG. 1, it can be readily seen that disease onset is delayed and there is less disease after 30 days when *Pseudomonas putida* is added to infested soil. A similar disease progress curve for radish is set forth in FIG. 2. This curve also shows a significant delay in disease onset, and less disease after 30 days when *Pseudomonas putida* is added to Fusarium wilt infected soil.

Figure 3:
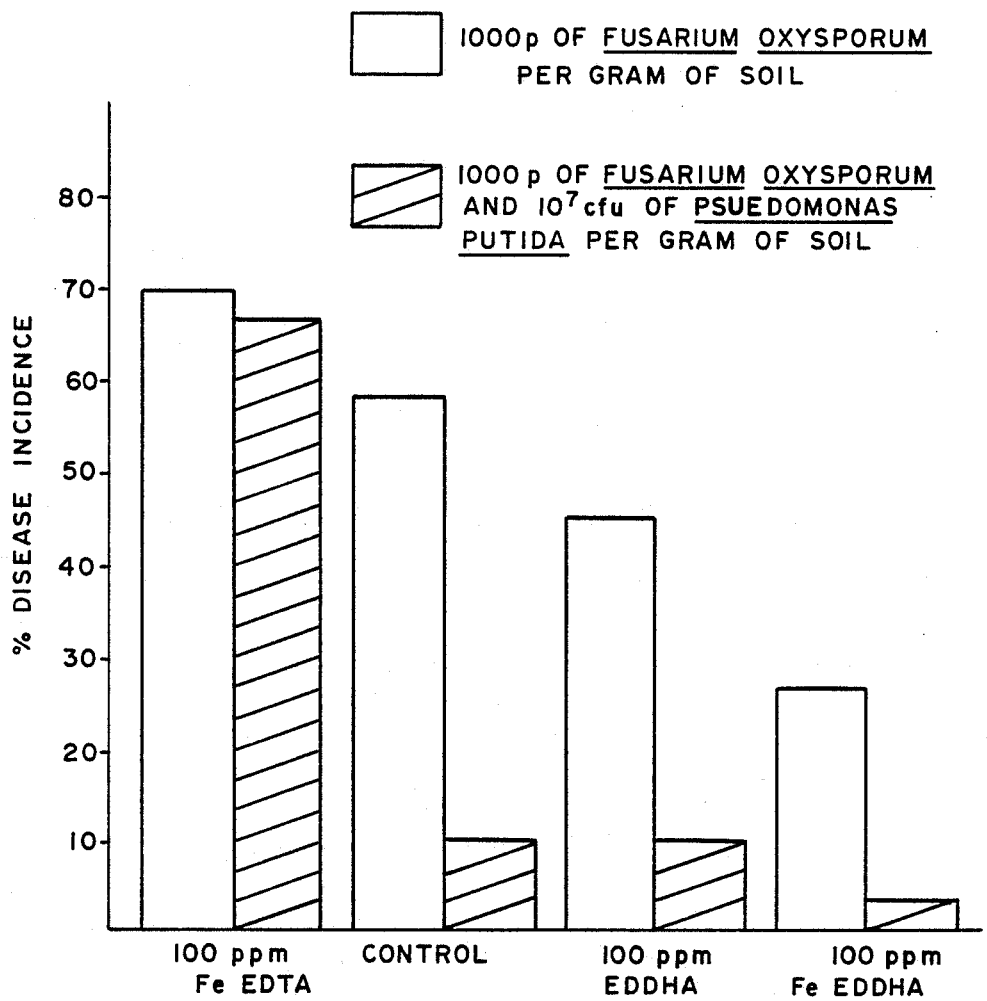
FIG. 3 is a bar graph of the incidence of Fusarium wilt of flax after 30 days.

FIG. 3 is a bar graph of mean flax wilt incidence after 30 days in eight soil treatment experiments. From FIG. 3, it is apparent that there was approximately 60% Fusarium wilt disease in the control which did not include *P. putida*, but only 10% disease when *P. putida* was added. This represents a six-fold decrease in disease incidence. FIG. 3 also indicates that when Fe-EDDHA or EDDHA was added to the soil either individually or in conjunction with *P. putida* there was significantly less disease than in the control. However, when Fe-EDTA is added to infected soil, disease was higher than in the control and no biological control occurred when Fe-EDTA is used in conjunction with *P. putida*.

EXAMPLE III

A series of experiments were conducted to evaluate the efficacy of FeEDDHA alone in the control of Fusarium wilt disease in cucumber, radish and flax. The procedures employed in isolating Fusarium wilt inoculum, and preparing pots for planting are as set forth in EXAMPLE I. The results of these experiments are set forth in TABLE II below. In Table II all results are significant at the 5% level.

TABLE II

| | Disease Incidence (%) | |
|---|---|---|
| Plant | Control | FeEDDHA (100 ppm) per g of soil |
| cucumber | 30 | 10 |
| Radish | 45 | 20 |
| Flax | 65 | 30 |

The results show that FeEDDHA exhibits significant disease control for Fusarium wilt disease in cucumber, radish and flax, providing a three-fold decrease in disease incidence when employed in amounts as little as 100 ppm per gram of soil.

EXAMPLES IV TO XXVII

A series of experiments are conducted which illustrate the *Fusarium oxysporum* disease suppressing properties of the disease suppressing strain of the microorganism *Pseudomonas putida* and a wide variety of ferric iron chelating agents and ferric iron chelates. In these experiments, the procedures employed are substantially identical to those described in the above EXAMPLE I. The results and physical parameters of these experiments are set forth in the following TABLE III.

TABLE III

| Example | Plant | Fusarium Wilt Suppressant and Amount/grams of Soil | Fusarium Wilt Disease Control |
|---|---|---|---|
| III | cucumber | 10³ cfu *P. putida* | good |
| IV | tomato | 10⁵ cfu *P. putida* | good |
| V | peas | 10⁴ cfu *P. putida* | good |
| VI | cotton | 10⁷ cfu *P. putida* | good |
| VII | bananas | 10⁸ cfu *P. putida* | good |
| VII | flax | 10⁹ cfu *P. putida* | good |
| IX | radish | 10¹² cfu *P. putida* | good |
| X | tomato | 50 ppm Ferric sodium ethylene diamine di-(o-hydroxy phenyl-acetate) | good |
| XI | peas | 75 ppm Sodium ethylene diamine di-(o-hydroxy phenylacetate) | good |
| X | flax | 200 ppm N,N'—di(2-aminoethyl ethylene-diamine) | good |
| XI | cotton | 2000 ppm N,N,N',N'— Tetra-(phosphomethyl) cyclohexane-,2-diamine | good |
| XII | radish | 10,000 ppm diethylene-triamine N,N,N', N", N"—pentaacetic acid | good |
| XIII | bananas | 500 ppm Ferric N—(o-hydroxy cyclohexyl) ethylenediamine-N,N', N'-triacetic acid | good |
| XIV | cucumber | 6,000 ppm 4,5-di-hydroxy 3-phenylazo-naphthalene-2,7-di-sulphonic acid | good |
| XV | flax | 8,000 ppm Ferric N,N'—ethylene di-(α-8d,8 - hydroxy phenyl) glycine | good |
| XVI | carnation | 800 ppm N,N'—ethylene di-[-N—(2-pyridylmethyl) glycine] | good |
| XVIII | cotton | 7,050 ppm Ferric 3,5-di sulfohydrocatechol | good |
| XIX | cucumber | 200 ppm Ferric ethylene bis-N,N'—(2-aminomethyl)-pyridine-N,N'—diacetic acid | good |
| XIX | radish | 4,000 ppm N—Hydroxyethyl-ethylene diamine diacetic acid | good |
| XX | peas | 500 ppm Ferric di-ethylenetriamine penta-acetic acid N,N—dihydroxy-ethylglycine | good |
| XXI | cotton | 6,000 ppm Sodium 2,3-di-hydroxy naphthalene-6-sulfonate | good |
| XXII | flax | 2,000 ppm Ferric di-sodium 1,2-dihydroxy benzene-3,5-disulfonate | good |
| XXIII | bean | 1,000 ppm 5-sulfosali- | good |

TABLE III-continued

| Example | Plant | Fusarium Wilt Suppressant and Amount/grams of Soil | Fusarium Wilt Disease Control |
|---|---|---|---|
| | | cylic acid | |
| XXIV | soybean | 750 ppm 8-hydroxy-5-methyl quinoline | good |
| XXV | peas | 250 ppm Ferric N,N'—di-(2-amino ethyl) ethylene diamine | good |
| XXVI | sweet potatoes | 350 ppm Ferric N,N—bis-(2-hydroxy ethylglycine) | good |
| XXVII | carnation | 750 ppm Ferric 2,3-dimercapto propan-1-ol | good |

What is claimed is:

1. A *Fusarium oxysporum* growth suppression composition which comprises a *Fusarium oxysporum* disease suppressive amount of at least one *Fusarium oxysporum* disease suppressant selected from the group consisting of a *Fusarium oxysporum* disease suppressive strain of *Pseudomonas putida* having the identifying characteristics of NRRL B-15001, and said *Fusarium oxysporum* disease suppressing strain of *Pseudomonas putida* in combination with a *Fusarium oxysporum* disease suppressing ferric iron chelating agent which forms a chelate whose stability is greater than the stability of the ferric iron chelate of ethylenediaminetetraacetic acid or the corresponding ferric iron chelate of said agent, and a biologically compatible carrier.

2. A composition according to claim 1 wherein said composition comprises a combination of said *Fusarium oxysporum* disease suppressing strain of *Pseudomonas putida* and at least one ferric iron chelating agent or the corresponding ferric iron chelate thereof.

3. A composition according to claim 2 wherein said combination includes a suppressant selected from the group consisting of chelating agents which form ferric iron chelates whose stabilities are equal to or greater than the stability of the ferric iron chelate of sodium ethylenediamine di-(o-hydroxy phenylacetate).

4. A composition according to claim 2 wherein said combination includes a suppressant selected from the group consisting of ferric iron chelating agents selected from the group consisting of oxalic acid, 2,3-dimercaptopropan-1-ol, cysteine, N,N'-di-(2-aminoethyl)ethylenediamine, pyridine-2-carboxylic acid, N,N-bis-(2-hydroxyethylglycine), 8-hydroxyquinazoline, 8-hydroxyquinoline, 5-bromo-8-hydroxyquinoline, 5-fluoro-8-hydroxyquinoline, 8-hydroxyquinoline-5-sulphonic acid, 8-hydroxy-7-idoquinoline-5-sulphonic acid, 5-cyano-8-hydroxyquinoline, 5-formyl-8-hydroxyquinoline, 8-hydroxy-5-methylquinoline, N,N,N',N'-tetra-(phosphomethyl)cyclohexane-1,2-diamine, ethyl 8-hydroxyquinoline-5-carboxylate, diethylenetriamine-N,N,N',N'',N''-pentaacetic acid, N-(o-hydroxy cyclohexyl) ethylenediamine-N,N',N'-triacetic acid, 4,5-dihydroxy-3-phenylazonaphthalene-2,7-disulphonic acid, N,N'-ethylene-di-(α-o-hydroxyphenyl)glycine, N,N'-ethylene di-[N-(2-pyridylmethyl)glycine], desferri-ferrioxamin B, desferri-ferrichrome, desferri-ferrioxamin E, N-acetyldesferri ferrioxamin B, iron free ferrichrome, desferriferrichrysin, 2'',6''-dichloro-4'-hydroxy-3,3'-dimethyl-3''-sulphofuchsome-5,5'-dicarboxylic acid, 3,5-disulfopyrocatechol, ethylene bis-N,N'-(2-aminoethyl)pyridine-N,N'-diacetic acid, N-hydroxyethylethylenediamine triacetic acid, diethylenetriamine pentaacetic acid, N,N-dihydroxyethylglycine, sodium 2,3-dihydroxynaphthalene-6-sulfonate, disodium 1,2-dihydroxy benzene-3,5-disulfonate and 5-sulfosalicylic acid, and ferric iron chelates thereof.

5. A composition according to claim 2 wherein said combination includes the suppressant sodium ethylenediamine di-(o-hydroxyphenylacetate).

6. A composition according to claim 1 wherein said carrier, is water.

7. A composition according to claim 1 which further comprises other biologically active materials.

8. A method of suppressing *Fusarium oxysporum* disease in *Fusarium oxysporum* conductive soil which comprises adding to said soil a *Fusarium oxysporum* disease suppressing amount of at least one suppressant selected from the group consisting of a *Fusarium oxysporum* disease suppressing strain of *Pseudomonas putida* having the identifying characteristic of NRRL B-15001, and said *Fusarium oxysporum* disease suppressing strain of *Pseudomonas putida* in combination with a *Fusarium oxysporum* growth suppressing ferric iron chelating agent which forms a chelate whose stability is greater than the ferric iron chelate of ethylenediaminetetraacetic acid or the corresponding ferric iron chelate of said agent.

9. A method according to claim 8 which comprises adding to said soil a combination of said strain of *Pseudomonas putida* and at least one additional suppressant selected from the group consisting of at least one ferric iron chelating agent and at least one ferric iron chelate.

10. A method of suppressing *Fusarium oxysporum* disease in *Fusarium oxysporum* conductive soil which comprises adding to said soil a *Fusarium oxysporum* disease suppressing amount of at least one suppressant selected from the group consisting of a *Fusarium oxysporum* disease suppressing strain of *Pseudomonas putida* having the identifying characteristic of NRRL B-15001 in combination with a *Fusarium oxysporum* growth suppressing ferric iron chelating agent which forms a chelate whose stability is greater than the ferric iron chelate of sodium ethylenediamine di-(o-hydroxy phenylacetate) or the corresponding ferric iron chelate of said agent.

11. A method according to claim 10 wherein said at least one chelating agent is selected from the group consisting of oxalic acid, 2,3-dimercapto-propan-1-ol, cysteine, N,N,'-di(2-aminoethyl) ethylenediamine, pyridine-2-carboxylic acid, N,N-bis-(2-hydroxyethyl-glycine), 8-hydroxyquinazoline, 8-hydroxyquinoline, 5-bromo-8-hydroxyquinoline, 5-fluro-8-hydroxyquinoline, 8-hydroxyquinoline5-sulphonic acid, 8-hydroxy-7-idoquinoline-5-sulphonic acid, 5-cyano-8-hydroxyquinoline, 5-formyl-8-hydroxy quinoline, 8-hydroxy-5-methyl quinoline, N,N,N',N'-tetra-(phosphomethyl)cyclohexane-1,2-diamine, ethyl 8-hydroxyquinoline-5-carboxylate, diethylenetriamine-N,N,N',N'',N''-pentaacetic acid, N-(o-hydroxycyclohexyl) ethylenediamine-N,N',N'-triacetic acid, 4,5-dihydroxy-3-phenylazonaphthalene-2,7-disulphonic acid, N,N'-ethylene-di-(α-o-hydroxyphenyl)glycine, N,N'-ethylene di-[N-(2-pyridylmethyl)glycine], desferri-ferrioxamin B, desferri-ferrichrome, desferri-ferrioxamin E, N-acetyl-desferri-ferroxamin B, iron free ferrichrome, desferriferrichrysin, 2'',6''-dichloro-4'-hydroxy-3,3'-dimethyl-3''-sulphofuchsome-5,5'-dicarboxylic acid, 3,5-disulfopyrocatechol, ethylene bis-N,N'-(2-aminomethyl)-pyridine-N,N'-diacetic acid, N-hydroxyethylethylenediaminetriacetic acid, diethylenetriaminepentaacetic acid, N,N-dihydroxyethylglycine, sodium 2,3-dihydroxy naphthalene-6-sulfonate, disodium 1,2-dihydroxybenzene-3,5-disulfonate and 5-sulfosalicylic acid.

12. A method according to claim 8 wherein said chelating agent is sodium ethylenediamine di-(o-hydroxy phenylacetate).

13. A method according to claim 8 which comprises adding to said soil a *Fusarium oxysporum* disease suppressive amount of said strain of *Pseudomonas putida*.

14. A method according to claim 13 which comprises inoculating the soil immediately surrounding a plant to be protected from *Fusarium oxysporum* with at least $10^3$ microorganism cells per gram of soil.

15. A method according to claim 14 wherein said soil is inoculated with at least about $10^7$ microorganism cells per gram of soil.

16. A method according to claim 15 wherein said soil is inoculated with at least about $10^9$ microorganism cells per gram of soil.

17. A method according to claim 16 wherein said soil is inoculated with at least about $10^{12}$ microorganisms per gram of soil.

18. A method according to claim 8 wherein the amount of said ferric iron chelating agent or the corresponding ferric iron chelate of said agent added to the soil, in combination with a *Fusarium oxysporum* disease suppressing strain of *Pseudomonas putida* having the identifying characteristic of NRRL B-15001, is added immediately surrounding the plant to be protected from *Fusarium oxysporum* and is at least about 50 parts-per-million per gram of soil.

19. A method according to claim 18 wherein said amount is at least about 100 parts-per-million per gram of soil.

20. A method according to claim 19 wherein said amount is in the range of from about 100 parts-per-million to about 10,000 parts-per-million per gram of soil.

21. A *Fusarium oxysporum* growth suppressing composition which comprises a biologically compatible carrier and a *Fusarium oxysporum* disease suppressive amount of at least one *Fusarium oxysporum* disease suppressant selected from the group consisting of a *Fusarium oxysporum* disease suppressing strain of *Pseudomonas putida* having the identifying characteristic of NRRL B-15001, and said *Fusarium oxysporum* disease suppressing strain of *Pseudomonas putida* in combination with EDDHA or FeEDDHA.

22. A composition according to claim 21 wherein said suppressants are selected from the group consisting of said strain of *Pseudomonas putida* having the identifying characteristics of NRRL B-15001 in combination with at least one *Fusarium oxysporum* disease suppressing ferric iron chelating agent and ferric iron chelate of such agent selected from the group consisting of EDDHA and FeEDDHA.

23. A composition according to claim 1 wherein said ferric iron chelating agent and corresponding ferric iron chelate is selected from the group consisting of Ferric sodium ethylene diamine di-(o-hydroxy phenyl acetate), N,N'-di(2-aminoethyl ethylene-diamine), N,N,N',N'-Tetra-(phosphomethyl) cyclohexane-2-diamine), diethylene-triamine N,N,N',N'',N''-pentaacetic acid, Ferric N-(o-hydroxy cyclohexyl) ethylenediamine-N,N',N'-triacetic acid, 4,5-di-hydroxy 3-phenylazo-naphthalene-2, 7-di-sulphonic acid, Ferric N,N'-ethylene di-(α-o-hydroxy phenyl) glycine, N,N'-ethylene di-[-N-(2-pyridylmethyl) glycine], Ferric 3,5-di sulfohyrocatechol, Ferric ethylene bis-N,N'-(2-aminomethyl)pyridine-N,N'-diacetic acid, N-Hydroxyethyl-ethylene diamine diacetic acid, Ferric di-ethylenetriamine pentaacetic acid N,N-dihydroxy-ethylglycine, Sodium 2,3-di-hydroxy naphthalene-6-sulfonate, Ferric di-sodium 1,2-dihydroxy benzene-3,5-disulfonate, 5-sulfosalicylic acid, 8-hydroxy-5-methyl quinoline, Ferric N,N'-di-(2-amino ethyl) ethylene diamine, Ferric N,N-bis-(2-hydroxy ethylglycine), and Ferric 2,3-dimercapto propan-1-ol.

24. A method according to claim 8 wherein said ferric iron chelating agent and corresponding ferric iron chelate is selected from the group consisting of Ferric sodium ethylene diamine di-(o-hydroxy phenyl acetate), N,N'-di(2-aminoethyl ethylene diamine), N,N,N',N'-Tetra-(phosphomethyl) cyclohexane-2-diamine, diethylene-triamine N,N,N',N'',N''-pentaacetic acid, Ferric N-(o-hydroxy cyclohexyl) ethylenediamine-N,N',N'-triacetic acid, 4,5-dihydroxy 3-phenylazo-naphthalene-2, 7-di-sulphonic acid, Ferric N,N'-ethylene di-(α-o-hydroxy phenyl) glycine, N,N'-ethylene di-[-N-(-2-pyridylmethyl) glycine], Ferric 3,5-di sulfohyrocatechol, Ferric ethylene bis-N,N'-(2-aminomethyl)-pyridine-N,N,-diacetic acid, N-Hydroxyethyl-ethylene diamine diacetic acid, Ferric diethylenetriamine pentaacetic acid N,N-dihydroxy-ethylglycine, Sodium 2,3-dihydroxy naphthalene-6-sulfonate, Ferric di-sodium 1,2-dihydroxy benzene-3,5-dihydroxy benzene-3,5-disulfonate, 5-sulfosalicylic acid, 8-hydroxy-5-methyl quinoline, Ferric N,N'-di-(2-amino ethyl) ethylene diamine, Ferric N,N-bis(2-hydroxy ethylglycine), and Ferric 2,3-dimercapto propan-1-ol.

25. A composition according to claim 21 wherein the *Fusarium oxysporum* disease suppressant is the *Fusarium oxysporum* disease suppressing strain of *Pseudomonas putida* having the identifying characteristic of NRRL B-15001.

* * * * *